US008492512B2

(12) United States Patent
Raiche et al.

(10) Patent No.: US 8,492,512 B2
(45) Date of Patent: Jul. 23, 2013

(54) PROCESS FOR REDUCING MOISTURE IN A BIODEGRADABLE IMPLANT DEVICE

(75) Inventors: Adrian Raiche, Helena, AL (US); Brandon Smith, Birmingham, AL (US); Kehley Miller, Bessemer, AL (US)

(73) Assignee: Surmodics Pharmaceuticals, Inc., Birmingham, AL (US)

( * ) Notice: Subject to any disclaimer, the term of this patent is extended or adjusted under 35 U.S.C. 154(b) by 0 days.

(21) Appl. No.: 13/221,429

(22) Filed: Aug. 30, 2011

(65) Prior Publication Data
US 2012/0077954 A1 Mar. 29, 2012

Related U.S. Application Data

(60) Provisional application No. 61/378,235, filed on Aug. 30, 2010, provisional application No. 61/378,134, filed on Aug. 30, 2010, provisional application No. 61/378,212, filed on Aug. 30, 2010, provisional application No. 61/380,937, filed on Sep. 8, 2010.

(51) Int. Cl.
*C08F 6/00* (2006.01)
*C08J 3/00* (2006.01)

(52) U.S. Cl.
USPC .......................... 528/480; 528/354

(58) Field of Classification Search
USPC ................. 528/354, 480
See application file for complete search history.

(56) References Cited

U.S. PATENT DOCUMENTS

| | | | |
|---|---|---|---|
| 4,020,558 A | 5/1977 | Cournut et al. | |
| 4,241,489 A | 12/1980 | Manning | |
| 4,704,692 A | 11/1987 | Ladner | |
| 4,804,691 A | 2/1989 | English et al. | |
| 4,892,736 A | 1/1990 | Goodson | |
| 4,898,734 A | 2/1990 | Mathiowitz et al. | |
| 5,004,602 A * | 4/1991 | Hutchinson | 514/7.6 |
| 5,278,201 A | 1/1994 | Dunn et al. | |
| 5,281,354 A | 1/1994 | Faber | |
| 5,407,609 A | 4/1995 | Tice et al. | |
| 5,468,253 A | 11/1995 | Bezwada et al. | |
| 5,514,378 A | 5/1996 | Mikos et al. | |
| 5,558,877 A | 9/1996 | Matlin et al. | |
| 5,599,552 A | 2/1997 | Dunn et al. | |
| 5,599,852 A | 2/1997 | Scopelianos et al. | |
| 5,702,717 A | 12/1997 | Cha et al. | |
| 5,705,716 A | 1/1998 | Chi | |
| 5,739,176 A | 4/1998 | Dunn et al. | |
| 5,759,563 A | 6/1998 | Yewey et al. | |
| 5,945,115 A | 8/1999 | Dunn et al. | |
| 6,006,122 A | 12/1999 | Smits | |
| 6,086,526 A | 7/2000 | Francischelli | |
| 6,126,919 A | 10/2000 | Stefely et al. | |
| 6,130,200 A | 10/2000 | Brodbeck et al. | |
| 6,331,311 B1 | 12/2001 | Brodbeck et al. | |
| 6,338,859 B1 | 1/2002 | Leroux et al. | |
| 6,413,536 B1 | 7/2002 | Gibson et al. | |
| 6,432,438 B1 | 8/2002 | Shukla | |
| 6,468,961 B1 | 10/2002 | Brodbeck et al. | |
| 6,469,132 B1 | 10/2002 | Eisenberg et al. | |
| 6,471,987 B1 | 10/2002 | McBride-Sakal et al. | |
| 6,477,428 B1 | 11/2002 | Skinner et al. | |
| RE37,950 E | 12/2002 | Dunn et al. | |
| 6,673,767 B1 | 1/2004 | Brodbeck et al. | |
| 6,845,352 B1 | 1/2005 | Wang | |
| 6,846,795 B2 | 1/2005 | Lant et al. | |
| 6,849,426 B2 | 2/2005 | Chen et al. | |
| 6,852,816 B2 | 2/2005 | Lewis et al. | |
| 6,923,985 B2 | 8/2005 | Peterson et al. | |
| 6,939,569 B1 | 9/2005 | Green et al. | |
| 7,053,209 B1 | 5/2006 | Gibson et al. | |
| 7,122,205 B2 | 10/2006 | Peterson et al. | |
| 7,128,927 B1 | 10/2006 | Dunn | |
| 7,299,905 B2 | 11/2007 | Yamaguchi et al. | |
| 2001/0000142 A1 | 4/2001 | Santos et al. | |
| 2002/0150622 A1 | 10/2002 | Philbrook et al. | |
| 2003/0114637 A1 | 6/2003 | Gogolewski | |
| 2003/0185872 A1 | 10/2003 | Kochinke | |
| 2003/0203991 A1 | 10/2003 | Schottman et al. | |
| 2004/0037885 A1 | 2/2004 | Seo et al. | |
| 2004/0052859 A1 | 3/2004 | Wu et al. | |
| 2005/0079202 A1 | 4/2005 | Chen et al. | |
| 2005/0129732 A1 | 6/2005 | Rubsamen | |
| 2005/0267543 A1 | 12/2005 | Heruth et al. | |
| 2006/0147491 A1 | 7/2006 | Dewitt et al. | |
| 2006/0212113 A1 | 9/2006 | Shaolian et al. | |

(Continued)

FOREIGN PATENT DOCUMENTS

| | | |
|---|---|---|
| EP | 0306212 | 3/1989 |
| EP | 1917971 | 5/2008 |

(Continued)

OTHER PUBLICATIONS

Gollwitzer, et al., "Antibacterial poly(D,L-lactic acid) coating of medical implants using a biodegradable drug delivery technology", Journal of Antimicrobial Chemotherapy, 2003, pp. 585-591.

Miller, et al., "Degradation Ratesof Oral Resorbable Implants (polylactates and polyglycolates): Rate Modification iwth Changes in PLA/PGA Copolymer Ratios", J. Biomed. Matr. Res. 11, 1977, pp. 711-719.

Mundargi, Raghavendra C. et al., "Development and evaluation of novel biodegradable microspheres based on poly(D,L-Lactide-co-glycolide) and poly(e-caprolactone) for controlled delivery of doxycyline in the treatment of human periodontal pocket: In vitro and in vivo studies", Journal of Controlled Release 119, 2007, pp. 59-68.

Bodansky and Trost, "Ed. Principles of Peptide Synthesis", Springer-Verlag, Inc, N.Y., 1993, (p. 1938-1942).

Beletsi, A et al., "Effect of Preparative Variables on the Properties of poly(dl-lactide-co-glycolide)—methoxypoly (ethyleneglycol) Copolymers Related to Their Applicaiton in Controlled Drug Delivery", International Journal of Pharmaceuticals, 182 (1999) pp. 187-197.

(Continued)

*Primary Examiner* — Terressa Boykin
(74) *Attorney, Agent, or Firm* — Pauly, Devires, Smith & Deffner, L.L.C.

(57) ABSTRACT

The disclosed process comprises freeze-drying a biodegradable implant device comprised or one or more polyesters to thereby reduce moisture content in the device.

7 Claims, 1 Drawing Sheet

U.S. PATENT DOCUMENTS

| | | |
|---|---|---|
| 2007/0005094 A1 | 1/2007 | Eaton et al. |
| 2007/0184084 A1 | 8/2007 | Chen et al. |
| 2007/0190154 A1 | 8/2007 | Zeigerson |
| 2007/0202145 A1 | 8/2007 | Ghabrial et al. |
| 2007/0207189 A1 | 9/2007 | Belcheva et al. |
| 2007/0265645 A1 | 11/2007 | Birk et al. |
| 2008/0118541 A1 | 5/2008 | Pacetti |
| 2008/0125728 A1 | 5/2008 | Bischoff et al. |
| 2008/0208323 A1 | 8/2008 | El-kurdi et al. |
| 2008/0260796 A1 | 10/2008 | Bischoff et al. |
| 2009/0124535 A1 | 5/2009 | Markland et al. |
| 2009/0198197 A1 | 8/2009 | Bischoff et al. |
| 2009/0306120 A1 | 12/2009 | Lim et al. |
| 2010/0098744 A1 | 4/2010 | Ferris et al. |
| 2010/0198278 A1 | 8/2010 | Cobian et al. |
| 2010/0203100 A1 | 8/2010 | Cobian et al. |
| 2010/0247596 A1 | 9/2010 | Bischoff |
| 2011/0098813 A1 | 4/2011 | Gibson |
| 2012/0077028 A1 | 3/2012 | Bowman et al. |
| 2012/0077887 A1 | 3/2012 | Bowman et al. |
| 2012/0078155 A1 | 3/2012 | Bowman et al. |

FOREIGN PATENT DOCUMENTS

| | | |
|---|---|---|
| EP | 2050474 | 4/2009 |
| EP | 2123312 | 11/2009 |
| WO | WO-9738676 | 10/1997 |
| WO | WO-2009064442 | 5/2009 |
| WO | WO-2010075298 | 7/2010 |
| WO | WO-2012030819 | 3/2012 |
| WO | WO-2012030821 | 3/2012 |
| WO | WO-2012030822 | 3/2012 |
| WO | WO-2012030823 | 3/2012 |

OTHER PUBLICATIONS

"Final Office Action", mailed Apr. 9, 2012 in co-pending U.S. Appl. No. 12/644,097, "Bioactive Terpolymer Compositions and Methods of Making and Using Same," (16 pages).

"Final Office Action", mailed Dec. 2, 2011 in co-pending U.S. Appl. No. 12/643,558, "Flexible Implantable Composites and Implants Comprising Same," (19 Pages).

"Final Office Action", mailed Jun. 3, 2011 in co pending U.S. Appl. No. 12/269,135, "Viscous Terpolymers as Drug Delivery Platform" (24 pages).

"Final Office Action", mailed May 18, 2012 in U.S. Appl. No. 12/643,546, "Elastic Implantable Composites and Implants Comprising Same," (11 pages).

"Final Office Action", mailed Oct. 28, 2011 in co-pending U.S. Appl. No. 12/643,571, "Implantable Suction Cup Composites and Implants Comprising Same," (22 pages).

"Final Office Action", mailed Sep. 27, 2012 in U.S. Appl. No. 12/643,580, "Bioactive Spray Coating Compositions and Methods of Making and Uses Thereof," (8 pages).

Hong, et al., "Generating Elastic, Biodegradable Poolyurethane/Poly(lactide-co-glycolide) Fibrous Sheets with Controlled Antibiotic Release via Two-Stream Electrospinning", Biomacromolecules, 9, 2008, pp. 1200-1207.

Nagy, et al., "Immunomodulation by tamoxifen and pergolide", Immunopharmacology, 12(2), Oct. 1986, (abstract only, pp. 1-2).

"International Search Report and Written Opinion", from International Application No. PCT/US2011/049726, corresponding to U.S. Appl. No. 13/221,389, mailed Nov. 18, 2011, pp. 1-11.

"International Search Report and Written Opinion", from International Application No. PCT/US2011/049730, corresponding to U.S. Appl. No. 13/221,415, mailed Nov. 18, 2011, pp. 1-20.

"International Search Report and Written Opinion", from International Application No. PCT/US2011/049731, corresponding to U.S. Appl. No. 13/221,429, mailed Feb. 14, 2012, pp. 1-9.

"International Search Report and Written Opinion", from International Application No. PCT/US2011/049735, corresponding to U.S. Appl. No. 13/221,464, mailed Nov. 18, 2011, pp. 1-15.

"Non-Final Office Action", mailed Aug. 3, 2011 in co-pending U.S. Appl. No. 12/643,558, "Flexible Implantable Composites and Implants Comprising Same," (27 pages).

"Non-Final Office Action", mailed Mar. 16, 2012 in co-pending U.S. Appl. No. 12/643,580, "Bioactive Spray Coating Compositions and Methods of Making and Uses Thereof," (31 Pages).

"Non-Final Office Action", mailed Oct. 11, 2011 in co-pending U.S. Appl. No. 12/644,097, "Bioactive Terpolymer Compositions and Methods of Making and Using Same" (48 pages).

"Non-Final Office Action", mailed Dec. 15, 2011 in co-pending U.S. Appl. No. 12/643,546, "Elastic Implantable Composites and Implants Comprising Same," (32 pages).

"Non-Final Office Action", mailed Sep. 20, 2012 in U.S. Appl. No. 12/644,097, "Bioactive Terpolymer Compositions and Methods of Making and Using Same," (38 pages).

"Non-Final Office Action", mailed Jan. 7, 2013 in co-pending U.S. Appl. No. 12/643,558, "Flexible Implantable Composites and Implants Comprising Same," (15 pages).

"PCT Notification Concerning Transmittal of International Preliminary Report on Nov. 21, 2011", Patentability from International Application No. PCTUS2009069024, corresponding to U.S. Patent Application No., mailed Jul. 7, 2011.

Kulkarni, et al., "Poly(lactic acid) for Surgical Implants", Technical Rep. 6608, Walter Reed Army Medical Center, Washington, D.C., 1966.

Stolnik, et al., "Polylactide-Poly(ethylene glycol) micellar-like Particles as Potential Drug Carriers: Production, Colloidal Properties and Biological Performance", J. Drug Targeting, 2001.

Sawhney, "Rapidly degraded terpolymers of dl-lactide, glycolide, and [epsilon]—caprolactone with increased hydrophilicity by copolymerization with ployethers", Journal of Biomedical Materials Research, Wiley, New York, NY, US vol. 24, No. 10, Oct. 1, 1990, pp. 1397-1411.

"Response to Final Office Action", mailed Aug. 20, 2012 in co-pending U.S. Appl. No. 12/643,546 9 pages.

"Response to Final Office Action", mailed Dec. 27, 2012 in U.S. Appl. No. 12/643,580, "Bioactive Spray Coating Compositions and Methods of Making and uses thereof", (5 pages).

"Response to Final Office Action", mailed Jan. 26, 2012 in co-pending U.S. Appl. No. 12/643,571, 11 pages.

"Response to Final Office Action", mailed Jul. 9, 2012 in U.S. Appl. No. 12/644,097, "Bioactive Terpolymer Compositions and Methods of Making an Dusing Same", (10 pages).

"Response to Final Office Action", mailed Mar. 2, 2012 in co-pending U.S. Appl. No. 12/643,558 10 pages.

"Response to Final Office Action", mailed Sep. 6, 2011 in U.S. Appl. No. 12/269,135, "Viscous Terpolymers As Drug Delivery Platform", 10 pages.

"Response to Non Final Office Action", mailed Jan. 3, 2012 in U.S. Appl. No. 12/644,097, "Bioactive Terpolymer Compositions and Methods of Making and Using Same", (8 pages).

"Response to Non Final Office Action", mailed Oct. 31, 2011 in U.S. Appl. No. 12/643,558, "Flexible Implantable Composites and Implants Comprising Same", (8 pages).

"Response to Non-Final Office Action", mailed Jun. 14, 2012 in co-pending U.S. Appl. No. 12/643,580 6 pages.

"Response to Non-Final Office Action", mailed Mar. 14, 2012 in co-pending U.S. Appl. No. 12/643,546, 8 pages.

"Response to Restriction Requirement", mailed Feb. 6, 2012 in co-pending U.S. Appl. No. 12/643,580, 5 pages.

"Restriction Requirement", mailed Jan. 6, 2012 in co-pending U.S. Appl. No. 12/643,580, "Bioactive Spray Coating Compositions and Methods of Making and Uses Thereof", 6 pages.

Mangkorn, Srisa-Ard et al., "Synthesis and characterization of a random terpolymer of L-lactide, e-caprolactone and glycolide", Society of Chemical Industry, Polymer International, vol. 50, Issue 8 (Jul. 20, 2001) pp. 891-896.

Sakkas, P. "The Future: Towards Long Acting Atypical Anti-Psychosis", Annals of General Hospital Psychiatry, Oral Presentation, Dec. 23, 2002, 1 pg.

* cited by examiner

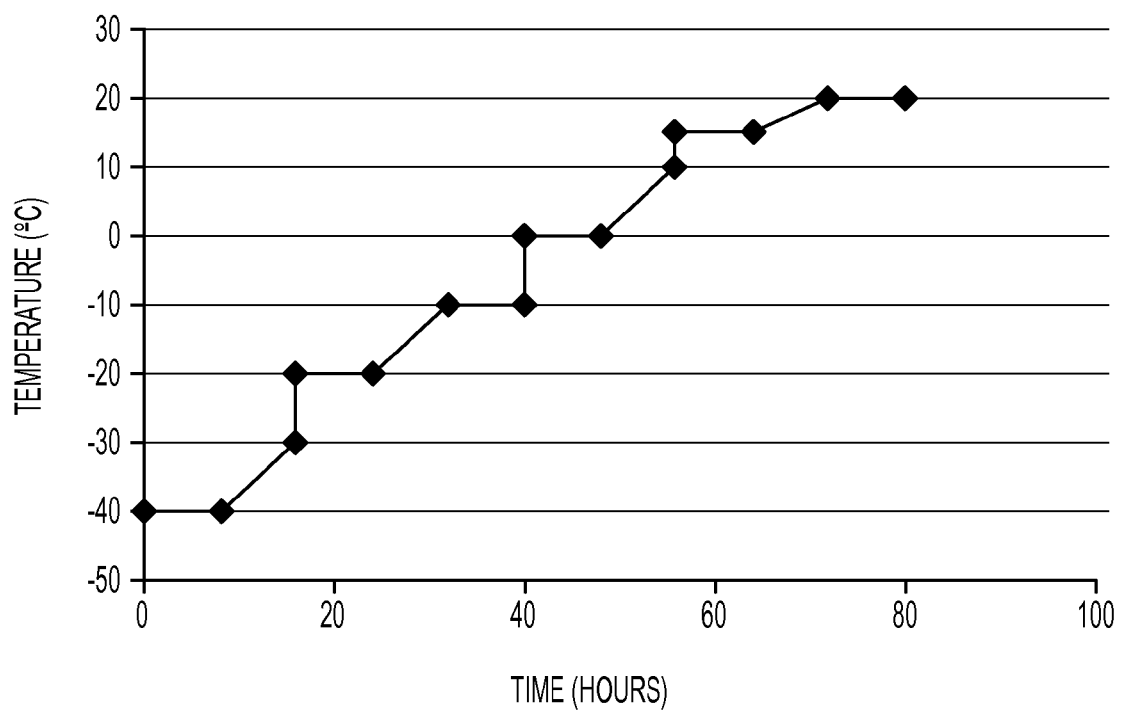

PROCESS FOR REDUCING MOISTURE IN A BIODEGRADABLE IMPLANT DEVICE

This application claims priority to U.S. Provisional Application No. 61/378,134, filed Aug. 30, 2010, U.S. Provisional Application No. 61/378,212, filed Aug. 30, 2010, U.S. Provisional Application No. 61/378,235, filed Aug. 30, 2010, and U.S. Provisional Application No. 61/380,937, filed Sep. 8, 2010, the content of all of which is herein incorporated by reference in its entirety.

BACKGROUND

Medical implant devices are often made from biodegradable polyesters, such as poly(lactide), poly(glycolide), poly(lactide-co-glycolide), and poly(caprolactone). Such devices can be implanted into a human or other subject to provide a wide variety of therapeutic benefits. The devices can help a bone to heal, deliver a drug, function as a fluid pump, stimulate electrical signals, as well as many other functions. Devices made from biodegradable polyesters provide the added advantage of being non-toxic and readily degradable and secretable from the subject once the lifetime of the device is over, or once the therapeutic effect is achieved. Biodegradable devices can be formulated so as to degrade over a relatively wide range of time periods, such as hours and up to months or even years.

Polyesters of biodegradable implant devices are susceptible to hydrolysis by water. Water can absorb into a device and thereby come in contact with the polyester even after a brief exposure of the device to a normal atmosphere. When water does come into contact with polyesters, hydrolysis is likely to occur. As a result of hydrolysis, polyesters breakdown or degrade into smaller subunits of the polymer. Such degradation, induced by hydrolysis, severely affects a number of properties of the device, such as the mechanical strength of the device, cohesiveness of the device, or can even cause the unwanted release of a substance, such as a drug, that is present within the device. Residual moisture resulting from a process for preparing a device or moisture that is later absorbed into the device can thus reduce the shelf-life of the device and adversely affect device performance.

SUMMARY

The disclosed process addresses the aforementioned problem of hydrolysis-induced degradation by effectively reducing moisture levels in biodegradable implant devices comprised of polyesters, such as poly(lactide), poly(glycolide), poly(lactide-co-glycolide), or poly(caprolactone).

The disclosed process comprises freeze-drying a biodegradable implant device comprised or one or more polyesters to thereby reduce moisture content in the device.

Also disclosed herein are implant devices comprising: poly(lactide), poly(glycolide), poly(lactide-co-glycolide), poly(caprolactone), or a copolymer thereof, and having a moisture content (water content) of 700 ppm or less in the device.

BRIEF DESCRIPTION OF THE DRAWINGS

FIG. 1 is plot of drying temperature versus time for a freeze-drying trial wherein a polymer film (implant device) comprising lactide, glycolide, and caprolactone polymers is lyophilized by freezing the film at a temperature of −40° C. followed by slowly increasing the temperature of the film to 20° C. over an 80 hour time period.

DETAILED DESCRIPTION

In this specification and in the claims that follow, reference will be made to a number of terms that have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

Singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The disclosed process comprises freeze-drying a biodegradable implant device to remove residual moisture from the device, while not adversely affecting the stability of the device by subjecting the device to high temperatures. Throughout the freeze-drying process, the device remains cool while freeze-dried water in the device sublimates under high vacuum.

During the freeze-drying process, the implant device can be exposed to the moisture vapor that is being removed from the device through sublimation. To decrease the moisture exposure time of the device, higher temperatures can be used. For example, a temperature that is above the glass transition temperature of the polymer of the device can be used as the freeze-drying temperature. As the freeze-drying temperature is increased, however, the likelihood for hydrolysis of the polyester is increased. Higher temperatures may also impact the stability of any pharmaceutically active substance present within the device.

A freeze-drying temperature under vacuum that keeps water frozen during the process is therefore ideal. The rate of hydrolysis of the polyester(s) in the device will be substantially slower when the water is frozen. Increasing the temperature under vacuum, while keeping the moisture frozen, thus leads to sublimation rather than evaporation of the moisture in the device. Sublimation is an endothermic process (heat-absorbing process), which allows for heat from the device to be absorbed, thus keeping the device cool and the remaining residual moisture in the device frozen.

The freeze-drying process can be carried out at a variety of temperatures and vacuum levels to ensure residual moisture in the device remains frozen while some of the moisture sublimates out of the device. The process can generally be carried out at temperatures ranging from −50° C. to 20° C. under high vacuum. The freeze-drying process can be carried out over a period of time ranging from 1 to 5 days. During the process, the freeze-drying temperature can remain the same or substantially the same, or can be changed over the course of the process. For example, a starting freeze-drying temperature of −50° C. can initially be used, and the freeze-drying temperature can be slowly increased up to 20° C. over time.

FIG. 1 shows a plot of drying temperature versus time for a freeze-drying trial wherein a polymer film (implant device) comprising lactide, glycolide, and caprolactone polymers is lyophilized by freezing the film at a temperature of −40° C. followed by slowly increasing the temperature of the film to 20° C. over an 80 hour time period.

The freeze-drying temperature used in the process can also be selected based on the glass-transition temperature of the polyester in the device. "Glass transition temperature" or "$T_g$," refers to the glass transition temperature as determined by differential scanning calorimetry (DSC). DSC defines the glass transition as a change in the heat capacity as the polymer goes from the glass state to the rubber state. This is a second order endothermic transition (requires heat to go through the transition), and thus the transition appears as a step transition, rather than a peak as would be expected with a melting transition.

For example, a poly(lactide-co-glycolide) or poly(lactide-co-caprolactone) device can be freeze dried at a constant temperature of 10° C. over a three day time period. A poly (caprolactone) device, by contrast, can be freeze-dried at a constant temperature of −5° C. over a three day time period. Less moisture is removed from a poly(caprolactone) device when the device is freeze-dried at a temperature of 10° C. over a three day time period. It is believed that this is at least partially due to differences in glass-transition temperatures between poly(caprolactone) and poly(lactide) based polymers.

It will be appreciated that devices processed in accordance with embodiments herein can include, but are not limited to, those including poly(lactide), poly(glycolide), poly(lactide-co-glycolide), poly(caprolactone), or copolymers thereof. Devices can specifically include terpolymers or blends of terpolymers including poly(lactide), poly(glycolide), and/or poly(caprolactone). In some embodiments, the device can include a poly(D,L-lactide-co-glycolide-co-ϵ-caprolactone) having a molecular weight ($M_w$) of 140,000 Daltons or less and a polydispersity index (PDI) of less than 2.0; wherein the poly(D,L-lactide-co-glycolide-co-ϵ-caprolactone) exhibits storage modulus (G') values of from about $1.5 \times 10^5$ Pa to about $5.5 \times 10^5$ Pa, over a frequency of from about 0.1 to about 1 Hz; and exhibits storage modulus (G') values of from about $1.0 \times 10^6$ Pa to about $4.0 \times 10^6$ Pa, over a frequency of from about $10^2$ to about $10^4$ Hz at 30° C. In some embodiments, the device can include a blend, comprising (a) a poly(D,L-lactide-co-glycolide-co-ϵ-caprolactone) having a molecular weight of from 75,000 to 250,000 Daltons and a polydispersity index (PDI) of less than 2.0, and (b) a poly(D,L-lactide-co-glycolide-co-mPEG) having a molecular weight of less than 25,000 Daltons and a polydispersity index (PDI) of less than 2.0; and wherein the weight ratio of the poly(D,L-lactide-co-glycolide-co-ϵ-caprolactone) to the poly(D,L-lactide-co-glycolide-co-mPEG) is from about 95:5 to about 75:25. In some embodiments, the device can include a blend comprising (a) a first poly(D,L-lactide-co-glycolide-co-ϵ-caprolactone) having a molecular weight (Mw) of from 75,000 to 250,000 Daltons and a polydispersity index (PDI) of less than 2.0, and (b) a second poly(D,L-lactide-co-glycolide-co-ϵ-caprolactone) having a molecular weight (Mw) of 130,000 Daltons or less and a polydispersity index (PDI) of less than 2.0, wherein the second poly(D,L-lactide-co-glycolide-co-ϵ-caprolactone) has a molecular weight (Mw) that is less than the first poly(D,L-lactide-co-glycolide-co-ϵ-caprolactone).

The process disclosed herein is useful for drying any implant device, formulation, or article comprising a polyester that is greater than 1 mm in length in at least one dimension of the device. Certain implant devices have a dimension that is from 1 mm to 50 mm, 1.2 mm to 45 mm, 1.4 mm to 42 mm, 1.6 mm to 40 mm, 1.8 mm to 38 mm, or 2.0 mm to 36 mm, 5.0 mm to 33 mm, or 10 mm to 30 mm. In a further aspect, the device has one dimension that is greater than 3 cm, even up to or greater than 10 cm, 20 cm, or even 30 cm. Each of these implant devices can be used with the disclosed process.

Virtually any type of implantable device comprised of the polyesters disclosed above can be dried using the disclosed process. The implant device can comprise any shape, such as a rod, a fiber, a cylinder, a bead, a ribbon, a disc, a wafer, a free-formed shaped solid, or a variety of other shaped solids. The device can have any regular or irregular shape and can have any cross section like circular, rectangular, triangular, oval, and the like. In one aspect, the device comprises a cylindrical disk-shape, such as a typical shape of an implantable pump.

The implant can be comprised of any suitable material in addition to the polyester, such as a metal (e.g., titanium), metal composite, organic material, polymeric, biodegradable, or even ceramic material. The surface of the implant can be any shaped surface, and may have a porous, beaded or meshed ingrowth surface, as can be present in certain implants.

As briefly discussed above, the implant device can be any type of medical implant. The implant devices can include, for example, implants for drug delivery, including drug delivery pumps; orthopedic implants, including spinal implants, implants for osseointegration or bone repair; medical stents, including stents with inherent drug delivery capability; prosthetic implants, including breast implants, muscle implants, and the like; dental implants; ear implants, including cochlear implants and hearing devices; cardiac implants including pacemakers, catheters, etc.; space filling implants; bioelectric implants; neural implants; internal organ implants, including dialysis grafts; defibrillators; monitoring devices; recording devices; stimulators, including deep brain stimulators, nerve stimulators, bladder stimulators, and diaphragm stimulators; implantable identification devices and information chips; artificial organs; drug administering devices; implantable sensors/biosensors; screws; tubes; rods; plates; or artificial joints.

Other implant devices that may benefit when used with the disclosed compositions include those with one or more active surfaces, e.g., a surface that enhances a connection between a tissue or fluid and the implant device, or a surface that allows for or enhances wound healing. The disclosed pressure-sensitive adhesives can be effective when applied to only a portion of the implant device, allowing for any active surface to remain exposed and functional when the implant device is implanted in a subject.

The implant device is "biodegradable," which refers to materials that will erode to soluble species or that will degrade under physiologic conditions to smaller units or chemical species that are, themselves, non-toxic (biocompatible) to the subject and capable of being metabolized, eliminated, or excreted by the subject.

The implant device can comprise a bioactive agent or drug. A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include those substances which affect the structure or function of a subject, or a pro-drug, which becomes bioactive or more bioactive after it has been placed in a predetermined physiological environment.

Examples of bioactive agents that can be incorporated into implant devices include generally any bioactive agents and particularly, thermally-labile bioactive agents. Thermally-labile bioactive agents are not likely to degrade when subjected to the freeze-drying processes disclosed herein.

Examples include without limitation small molecules, peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents.

Other bioactive agents can include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, antipsychotics, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Still other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestyramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents include, but are not limited to, peptide drugs, protein drugs, therapeutic antibodies, anticalins, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, anti-inflammatory agents, nonsteroidal anti-inflammatory agents, antiparkinsonian agents, antihypertensive agents, β-adrenergic blocking agents, nutritional agents, anti-TNF agents and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; antipsychotics such as clozapine, haloperidol, carbamazepine, gabapentin, topimarate, bupropion, sertraline, alprazolam, buspirone, risperidone, aripiprazole, olanzapine, quetiapine, ziprasidone, iloperidone, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin B12, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni,* and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

EXAMPLE 1

Three separate sets of polymer film samples are prepared by compressing the polymer film and subsequently cutting the film into 1 inch diameter circles. The compressed and cut films (implant devices) are equilibrated at 100% relative humidity at room temperature and then freeze-dried under high vacuum for 3 days at one of three constant temperatures: −20° C., −5° C., or 10° C. The moisture content of the devices is then determined and compared to moisture content of the same devices after a vacuum drying process. Table 1 shows the results.

TABLE 1

| | Water content (ppm) | | |
|---|---|---|---|
| Polymer | Control (before drying) | Vacuum dried | Freeze-dried |
| Poly(lactide-co-glycolide) (85 mol % lactide, 15 mol % glycolide) | 6674 | 1071 | 549 |
| Poly(lactide-co-caprolactone) (75 mole % lactide, 25 mol % caprolactone) | 4628 | 710 | 111 |
| Poly(caprolactone) | 3693 | 1555 | 664 |

As can be seen from the results, the freeze-drying process reduces moistures levels substantially relative to the more conventional vacuum drying.

Various modifications can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. A process for reducing moisture content in a biodegradable implant device comprising freeze-drying the biodegradable implant device to thereby reduce moisture content in the device; wherein the implant device comprises poly(lactide), poly(glycolide), poly(lactide-co-glycolide), poly(caprolactone), or a copolymer thereof.

2. The process of claim 1, comprising cooling the device at a temperature ranging from −50° C. to 20° C. under high vacuum for a period of time ranging from 1 to 5 days.

3. The process of claim 1, comprising initially cooling the device at a starting temperature of from −50° C. to −20° C. under high vacuum followed by warming the device at a temperature of up to 20° C. under high vacuum over a time period ranging from 1 to 5 days.

4. The process of claim 1, wherein moisture content is reduced by at least 80%.

5. The process of claim 1, wherein the device comprises an initial moisture content ranging from 2,000 to 8,000 parts per million water by weight of the device.

6. An implant device comprising: poly(lactide), poly(glycolide), poly(lactide-co-glycolide), poly(caprolactone), or a copolymer thereof, and having a moisture content of 700 ppm or less in the device.

7. A process for delaying hydrolysis in a biodegradable implant device comprising freeze-drying the biodegradable implant device to thereby reduce moisture content in the device; wherein the implant device comprises poly(lactide), poly(glycolide), poly(lactide-co-glycolide), poly(caprolactone), or a copolymer thereof.

* * * * *